United States Patent [19]

Lam et al.

[11] Patent Number: 5,036,010
[45] Date of Patent: Jul. 30, 1991

[54] BMY-40800 ANTITUMOR ANTIBIOTICS

[75] Inventors: King S. Lam, Cheshire; Jacqueline Mattei, East Haven; John E. Leet; James A. Matson, both of Cheshire, all of Conn.; Koji Tomita, Tokyo, Japan; Murray A. Kaplan, Syracuse, N.Y.

[73] Assignee: Bristol-Myers Company, New York, N.Y.

[21] Appl. No.: 515,006

[22] Filed: Apr. 26, 1990

Related U.S. Application Data

[62] Division of Ser. No. 155,778, Feb. 16, 1988, Pat. No. 4,994,271.

[51] Int. Cl.[5] .............................................. C12N 1/20
[52] U.S. Cl. .................................. 435/253.5; 435/898
[58] Field of Search ............................. 435/253.5, 898

[56] References Cited

U.S. PATENT DOCUMENTS 3,875,006  4/1975  Belloc et al. .................. 435/816
4,415,669 11/1983  Hernandez ..................... 435/898
4,504,580  3/1985  Hanada et al. .................. 435/898

OTHER PUBLICATIONS

*Bergey's Manual of Determinative Bacteriology*, 8th ed. 1974.

Primary Examiner—Johannie R. Brown
Assistant Examiner—Pamela S. Webber
Attorney, Agent, or Firm—David M. Morse

[57] ABSTRACT

A new antitumor antibiotic designated BMY-40800 is produced by fermentation of *Streptomyces hygroscopicus* ATCC 53653. The new compound inhibits the growth of tumors in experimental animals.

1 Claim, 3 Drawing Sheets

13C NMR SPECTRUM OF BMY-40800 (CDCl3)

BMY-40800 ANTITUMOR ANTIBIOTICS

This application is a division of co-pending application Ser. No. 155,778, filed Feb. 16, 1988, now U.S. Pat. No. 4,994,271.

BACKGROUND OF THE INVENTION

1. Field of the Invention

This invention relates to a novel antitumor antibiotic and to its production and recovery.

2. Description of the Prior Art

The structure of BMY-40800, the antitumor antibiotic of the present invention, has not yet been elucidated. However, based on the characterizing properties of the compound, it is believed that BMY-40800 is a novel compound.

SUMMARY OF THE INVENTION

In accordance with one aspect of the present invention, there is provided the antibiotic substance BMY-40800 which demonstrates both in vitro and in vivo antitumor activity.

In accordance with another aspect of the invention, there is provided a process for preparing BMY-40800 which comprises cultivating a BMY-40800-producing strain of *Streptomyces hygroscopicus*, preferably strain C39108-P210-51 (ATCC 53653) or a BMY-40800-producing variant or mutant thereof, in an aqueous nutrient medium containing assimilable sources of carbon and nitrogen under submerged aerobic conditions until a substantial amount of BMY-40800 is produced by said organism in said culture medium and then recovering the BMY-40800 from said culture medium.

In accordance with another aspect of the invention, there are provided pharmaceutical compositions containing an effective tumor-inhibiting amount of BMY-40800 in combination with a pharmaceutical carrier or diluent.

In yet another aspect of the invention, there is provided a method for therapeutically treating a mammalian host affected by a malignant tumor which comprises administering to said host an effective tumor-inhibiting amount of BMY-40800 or pharmaceutical composition thereof.

DETAILED DESCRIPTION

Figure 1:
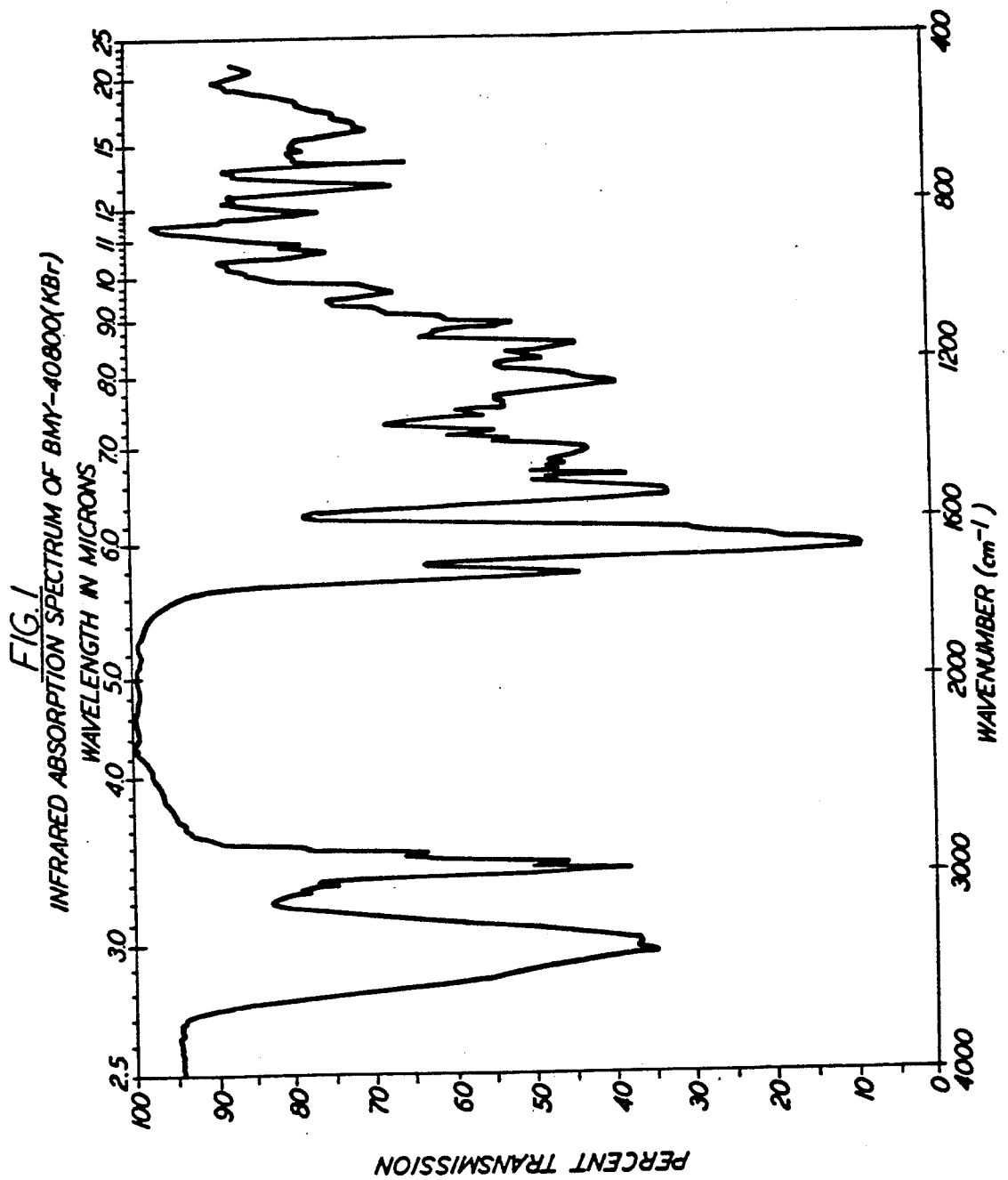
FIG. 1 represents the infrared absorption spectrum of BMY-40800 (KBr pellet).
Figure 2:
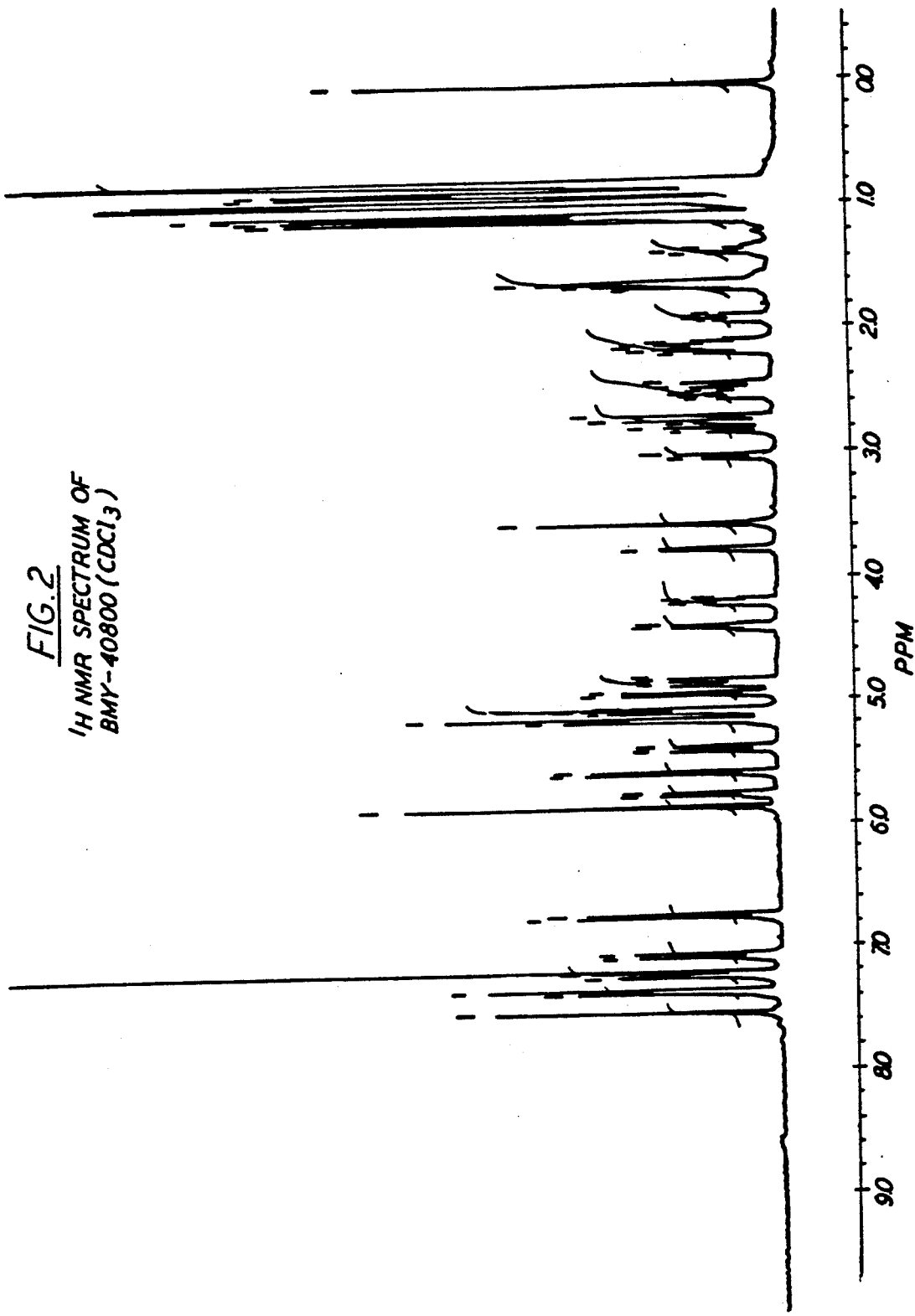
FIG. 2 represents the 360 MHz proton magnetic resonance spectrum of BMY-40800 in $CDCl_3$.

The BMY-40800 antibiotic of the present invention is produced by fermentation of a BMY-40800-producing strain of Streptomyces. The preferred producing organism is a novel strain of *Streptomyces hygroscopicus* designated herein as *Streptomyces hygroscopicus* strain C39108-P210-51. This strain was isolated from a soil sample collected at Himachal Pradesh State, India. A biologically pure culture of strain C39108-P210-51 has been deposited with the American Type Culture Collection, Rockville, Md., and added to their permanent collection of microorganisms as ATCC 53653. This culture, designated as C39108, is also maintained as a dormant culture in lyophile tubes and cryogenic vials in the Bristol-Myers Pharmaceutical Research and Development Division Culture Collection, 5 Research Parkway, Wallingford, Conn. 06492.

The results of taxonomic studies performed on strain C39108-P210-51 indicate that the strain is a novel strain of *Streptomyces hygroscopicus*.

Strain C39108 has the following properties as determined by materials and procedures described by Shirling and Gottlieb (Int. J. Syst. Bacteriology 16: 313–340, 1966; ibid. 18: 69–189, 1968; ibid. 22: 265–394, 1972), Staneck and Roberts (Appl. Microbiol. 28, 226–31, 1974), K.P. Schall (M. Goodfellow and D.E. Minnikin Eds, Chemical Methods in Bacterial Systematics, Academic Press Inc., pp. 359–381, 1985).

Morphology

Both substrate and aerial mycelia are formed, which are long, well-branched and not fragmented into short filaments. Chains of arthrospores are born on the aerial hyphae. The spore chain and spore morphology are as follows: 1) spiral spore chains with 2 to 8 turns, 2) monopodially branched sporophores, 3) spores, oval or barrel-shaped (0.5 to 0.7 by 0.5 to 1.2 $\mu m$), and 4) spore ornamentation, rugose or smooth. Sporangium, motile spore and sclerotium are not observed.

Cultural and Physiological Characteristics

Strain C39108 grows well in most descriptive media. The aerial mycelium shows grayish color after sporulation and occurs as blackish moistening patches (hygroscopic change) in ISP media No. 2, 4 and 7 and Bennett's agar. The substrate mycelium is colorless, grayish yellow or olive brown. Production of melanoid pigments was negative on peptone-yeast extract-iron and tyrosine agars and in tryptone-yeast extract broth. The carbon utilization pattern of strain C39108-P210-51 was determined by the method of Shirling and Gottlieb (*Int. J. Syst. Bacterial*, 16: 313–340, 1960) excepting the inclusion of a three hour starvation period between the harvesting and inoculation steps. Washed vegetative cells were shaken at 250 rpm on a rotary shaker in a liquid version of ISP medium No. 9 with no carbon source. As summarized in Table 1, positive utilization of rhamnose, fructose, glycerol, xylose, lactose, galactose, glucose, and sucrose, among others, was observed.

The cultural and physiological characteristics of strain C39108-P210-51 are summarized in Tables 2 and 3.

TABLE 1

| Carbon Utilization, Strain C39108-P210-51 | | |
|---|---|---|
| Best Utilization: | Rhamnose | |
| | Soluble Starch | |
| | D-fructose | |
| Moderate Utilization: | Glycerol | Sucrose |
| | D-xylose | Trehalose |
| | Lactose | D-mannitol |
| | D-galactose | Raffinose |
| | D-glucose | L-arabinose |
| Doubtful Utilization: | i-Inositol | |
| | Melibiose | |
| Negative Utilization: | Maltose | Melezitose |
| | Sorbose | D-ribose |
| | Dulcitol | D-arabinose |
| | Salicin | Cellobiose |
| | D-mannose | |

TABLE 2

Cultural Characteristics of Strain C39108-P210-51

| Medium | | Description |
|---|---|---|
| Tryptone-Yeast extract broth (ISP 1) | G: | moderate, not turbid |
| | R: | |
| | A: | none |
| | P: | none |
| Yeast-extract - Malt extract agar (ISP 2) | G: | moderate |
| | R: | mustard brown, [5;E6] |
| | A: | black |
| | P: | brown, [6;E5] |
| Oatmeal agar (ISP 3) | G: | scant |
| | R: | cream, [4;A3] to gray |
| | A: | black |
| | P: | none |
| Inorganic salts - Starch agar (ISP 4) | G: | scant |
| | R: | cream, [4;A3] to gray |
| | A: | black |
| | P: | none |
| Glycerol - Asparagine agar (ISP 5) | G: | fair to moderate |
| | R: | sand, [4;B3] |
| | A: | scant, gray and white |
| | P: | none |
| Peptone-Yeast extract - Iron agar (ISP 6) | G: | poor, flat |
| | R: | butter yellow, [4;A5] |
| | A: | none |
| | P: | none |
| Tyrosine agar (ISP 7) | G: | scant |
| | R: | cream, [4;A3] |
| | A: | none |
| | P: | apricot (yellow), [5;B6] |
| Czapek's Sucrose - Nitrate agar | G: | fair |
| | R: | ivory to champagne [4;B(3-4)] |
| | A: | scant, gray and white |
| | P: | grayish orange [5;B3] |
| Glucose - Asparagine agar | G: | fair to moderate |
| | R: | champagne [4;B4] |
| | A: | scant, gray and white |
| | P: | slight, natural [4;A3] |
| Skim milk agar | G: | fair, raised, convoluted |
| | R: | cream, [4;A3] |
| | A: | none |
| | P: | none |
| Maltose-Tryptone agar | G: | moderate, raised |
| | R: | yellowish white [4;A2] |
| | A: | none |
| | P: | none |
| Nutrient agar | G: | fair |
| | R: | dull yellow [3;B3] |
| | A: | scant, gray and white |
| | P: | none |
| Tomato juice agar | G: | good, raised |
| | R: | brownish orange [6;C8] |
| | A: | none |
| | P: | slight, light brown [6;D8] |
| Casein - Starch agar | G: | scant, ivory, flat |
| | R: | yellowish white [4;A2] |
| | A: | none |
| | P: | none |
| Modified Bennett's agar | G: | moderate, raised |
| | R: | cream, [4;A3] |
| | A: | none |
| | P: | light yellow [4;A4] | o Observed after incubation at 28° C. for 2 weeks
oo Abbreviations:
G = growth
R = reverse color
A = aerial mycelium
P = diffusible pigment
ooo Color names and numbers (in brackets) from "Reinhold Color Atlas, by A. Kornerup and J. H. Wanscher, Reinhold Publishing Corporation, 1961, by Politikens Forlag, Copenhagen, Denmark".

TABLE 3

Physiological Characteristics of Strain C39108-P210-51

| | |
|---|---|
| Hydrolysis of: | |
| Gelatin | + |
| Starch: | |
| Soluble starch | + |
| Potato starch | − |
| Milk coagulation | − |
| peptonization | + |
| Production of: | |
| Nitrate reductase | − or +*[1] |
| Tyrosinase | − |
| Tolerance to: | |
| Lysozyme, | |
| 0.01% (w/v) | − |
| 0.001% (w/v) | − |
| NaCl, | |
| 1%–8% (w/v) | + |
| 10% (w/v) | − |
| pH, | |
| 5.0–11.0 | + |
| 4.5 and 12 | − |
| Temperature: | |
| Growth range | 18° C.–39° C. |
| No growth | 15° C. and 41° C. |
| Optimal growth | 30° C.–34° C. |

*[1] Negative in Czapek's sucrose-nitrate broth and positive in peptone-nitrate broth

Cell Wall Chemistry

The whole cell wall hydrolyzate shows the presence of LL-diaminopimelic acid and ribose. The phospolipids contain phosphatidylethanolamine, phosphatidylglycerol and phosphatidylinostol, hence belong to the type P-II.

The morphological, cultural and physiological characteristics and cell chemistry of strain C39108 indicate that the strain belongs to the species, *Streptomyces hygroscopicus*. The major characteristics of the strain are summarized as follows: 1) gray aerial mycelium, 2) spore chain, Spirales, 3) non-chromogenic (melanin negative), 4) smooth spore wall ornamentation and (5) hygroscopic change of sporulated aerial mycelium.

Since the Streptomyces are easily mutated naturally or artificially, the present invention includes within its scope *Streptomyces hygroscopicus* strain C39108-P210-51 (ATCC 53653) and all BMY-40800-producing natural variants or mutants which can be produced from the described organism by conventional means such as UV radiation, x-rays, nitrogen mustard oils, etc. and genetic engineering means.

Antibiotic Production

The BMY-40800 antibiotic of the present invention is prepared by cultivating a BMY-40800-producing strain of *Streptomyces hygroscopicus*, preferably a strain of *Streptomyces hygroscopicus* having the identifying characteristics of strain C39108-P210-51 (ATCC 53653), or a mutant or variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate carbon source such as sucrose, lactose, glucose, rhamnose, fructose, glycerol or soluble starch. An assimilable nitrogen source such as fish meal, peptone peanut meal, cottonseed meal or cornsteep liquor should also be employed. Nutrient inorganic salts can also be incorporated in the medium so as to provide sodium, potassium, ammonium, calcium, phosphate, sulfate, chloride, bromide, nitrate, carbonate and like ions.

Production of BMY-40800 can be effected at any temperature conducive to satisfactory growth of the producing organism, e.g. 18° C. to 39° C. and is conveniently carried out at a temperature of about 28° C.

The fermentation may be carried out in flasks or in laboratory or industrial fermentors of various capacity. When tank fermentation is to be used, it is desirable to produce a vegetative inoculum in a nutrient broth by inoculating a small volume of the culture medium with a slant or a lyophilized culture of the producing organism. After obtaining a viable and active inoculum in this manner, it is transferred aseptically to the fermentation tank medium for large scale production of BMY-40800. The medium in which the vegatative inoculum is produced can be the same as, or different from, that utilized in the tank as long as it is such that a good growth of the producing organism is obtained. Antibiotic production may be monitored by high performance liquid chromatography assay or by a conventional biological assay. In general, optimum production of BMY-40800 is achieved after incubation of about five days.

Isolation and Purification

BMY-40800 is the major product of the fermentation and may be recovered from the culture medium and isolated in a substantially pure form according to the procedure described in Example 2 below. Scheme 1 below illustrates a preferred isolation procedure.

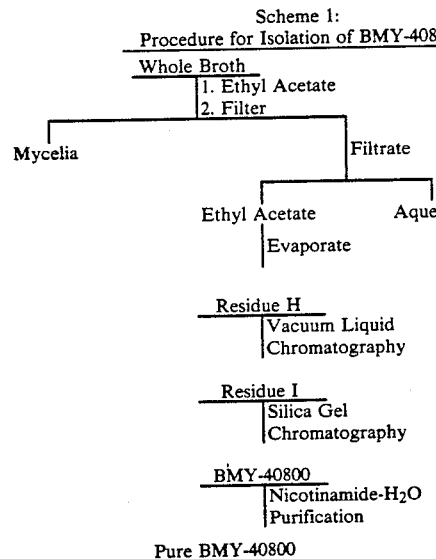

Scheme 1:
Procedure for Isolation of BMY-40800

Pure BMY-40800

Physicochemical Properties of BMY-40800

The physicochemical properties of BMY-40800 are as follows:

Description: white crystalline solid
Molecular formula: $C_{72}H_{104}N_{14}O_{20}$
Elemental analysis: C, 58.16; H, 6.94; N, 12.84
Molecular weight: 1484
Mass spectrum: V.G.70 SE double focusing mass spectrometer, $[M]^+$ 1484, $[M+H]^+$ 1485, $[M+Na]^+$ 1507, $[M+K]^+$ 1523.
Infrared spectrum: Perkin Elmer 1800 Fourier Transform, IR spectrometer, KBr pellet, Major IR bands ($cm^{-1}$): 3393, 3335, 2965, 2932, 2876, 1731, 1675, 1630sh, 1532, 1484, 1469, 1454, 1422, 1392, 1372, 1330, 1308, 1250, 1187, 1154, 1101, 1019, 918, 898, 817, 757 and 609

Ultraviolet spectrum: Hewlett-Packard 8452A Diode Array, Spectrophotometer, Concentration 0.01538 g/l methanol, 286 nm [0.2891(a)]log$\epsilon$=4.45

Analytical HPLC: K'=8.9 Column: Whatman Partisil 10 ODS-3 (1P4712), Eluant: 4 parts acetonitrile 1 part tetrahydrofuran, 5 parts water; Flow: 2 ml/min; Detector: 293 nm; Retention Time: 15 minutes; Sample concentration: 1 μg/μl DMSO 360 MHz $^1$H NMR: Bruker Model WM-360 spectrometer; Solvent: $CDCl_3$ Observed chemical shifts (relative to chloroform signal 7.2403): 0.83 (t,3H), 0.83 (t,3H), 0.88 (d,3H), 0.96 (d,3H), 0.96 (d,3H), 1.08 (d,3H), 1.11 (d,3H), 1.35 (m,1H), 1.64 (m,2H), 1.92 (m,1H), 2.12 (m,2H), 2.44 (d,1H), 2.52 (m,1H), 2.70 (d,1H), 2.79 (t,1H), 3.02 (d,1H), 3.40 (s,1H), 3.59 (s,1H), 3.77 (s,1H), 4.18 (m,1H), 4.40 (q,1H), 4.84 (d,1H), 4.94 (d,1H), 5.08 (m,1H), 5.11 (m,1H), 5.16 (m,1H), 5.37 (d,1H), 5.62 (d,1H), 5.78 (m,1H), 5.89 (s,1H), 6.74 (d,1H), 7.08 (d,1H), 7.25 (m,1H), 7.31 (d,1H), 7.38 (d,1H), 7.52 (d,1H).

$^{13}$C NMR: Bruker Model WM-360 spectrometer Solvent: $CDCl_3$; Observed chemical shifts (relative to chloroform signals δ76.55, 76.90, 77.25):

| Signal | PPM | Multiplicity |
| --- | --- | --- |
| 1 | 16.33 | q |
| 2 | 17.26 | q |
| 3 | 18.18 | q |
| 4 | 18.79 | q |
| 5 | 19.25 | q |
| 6 | 20.90 | q |
| 7 | 22.86 | q |
| 8 | 25.21 | d |
| 9 | 28.54 | t |
| 10 | 29.81 | d |
| 11 | 29.89 | d |
| 12 | 39.37 | t |
| 13 | 40.86 | t |
| 14 | 49.83 | d |
| 15 | 52.55 | t |
| 16 | 53.72 | d |
| 17 | 54.19 | d |
| 18 | 57.10 | d |
| 19 | 58.59 | d |
| 20 | 60.70 | d |
| 21 | 66.58 | d |
| 22 | 77.11 | d |
| 23 | 86.10 | d |
| 24 | 90.76 | s |
| 25 | 112.48 | d |
| 26 | 121.29 | d |
| 27 | 128.30 | d |
| 28 | 132.20 | s |
| 29 | 134.31 | s |
| 30 | 146.56 | s |
| 31 | 172.23 | s |
| 32 | 172.90 | s |
| 33 | 173.14 | s |
| 34 | 173.34 | s |
| 35 | 173.78 | s |
| 36 | 173.96 | s |

Thin layer chromatography: $R_f$0.35 Plate: Uniplate Silica Gel GHLF, 0.25 mm thickness (Analtech) Mobile phase: Chloroform-methanol (95:5 v/v) Detection: turns yellow upon standing in air turns orange with ceric sulfate spray reagent at room temperature Composition: Compounds contains amino acids valine, leucine and threonine in equimolar amounts. Also present is α-hydroxyisovaleric acid.

Biological Activity of BMY-40800

BMY-40800 was tested against the transplanted mouse leukemia P-388 to determine in vivo antitumor activity. The procedure employed and the results are presented below.

Procedure:

$CDF_1$ mice were implanted intraperitoneally (ip) with $10^6$ P388 leukemia cells obtained from DBA/2 donor mice bearing this transplantable murine leukemia. The $CDF_1$ leukemic mice were treated ip with either saline (control mice) or doses of BMY-40800 once daily for five consecutive days beginning one day post-tumor inoculation. These animals were observed daily and their deaths recorded. Average body weight changes (from the day of leukemia implant to the day of last treatment) were determined for all groups as a means of reflecting drug toxicity. The incidence of mice alive in each group on Day 5 post-tumor implant was recorded as an additional means of assessing drug toxicity. No therapeutic result was considered as meaningful if more than one mouse per treatment group had died by Day 5. Treatment groups consisted of either 4 or 6 mice; control groups contained 10 mice. The number of mice, if any, surviving to Day 30 (the last day of the experiments) was also recorded.

Therapeutic efficacy was evaluated by determining the median survival time (MST) of BMY-40800-treated mice and comparing it to the MST of parallel control mice. This comparison was made by dividing the MST of the former by the latter and multiplying by 100 to derive a parameter called the percent T/C value. A percent T/C of $\geq 125\%$ was considered to represent a meaningful increase in lifespan and hence an active result.

Results: BMY-40800 was evaluated in two experiments, the data for which are shown in Table 4. In this first experiment (#8016), the highest dosage tested, 1 mg/kg/inj for five consecutive daily ip injections, yielded a T/C of 135%. There were no deaths noted by Day 5 and no survivors by Day 30.

In the second study (#8023), the highest dosage evaluated, 3.2 mg/kg/inj for five injections, caused the death of two (of six) mice by Day 5 and so was considered too toxic a dose level. The best effect was achieved at a dosage of 0.8 mg/kg/inj and consisted of a T/C of 140%.

Thus, in two experiment versus P388 leukemia, BMY-40800 achieved increases in lifespan reflective of active results at tolerated dosages.

As indicated by the data provided above, BMY-40800 is useful as an antitumor agent for the inhibition of mammalian malignant tumors such as P-388 leukemia.

The invention includes within its scope pharmaceutical compositions containing an effective tumor-inhibiting amount of BMY-40800 in combination with an inert pharmaceutically acceptable carrier or diluent. Such compositions may contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or other sterile injectable medium immediately before use.

For use as an antitumor agent, optimal dosages and regimens of BMY-40800 for a given mammalian host can be readily ascertained by those skilled in the art. It will, of course, be appreciated that the actual dose of BMY-40800 used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided to enable one skilled in the art to practice the present invention. They are not to be construed as limiting the scope of the invention. Unless otherwise indicated the percentages given are percentage by weight and ratios of liquids are volume/volume.

Example 1

Fermentation of BMY-40800

A. Shake-flask fermentation

Strain C39108-P210-51 (ATCC 53653) was maintained and transferred in test tubes on agar slants of yeast-malt extract agar. This medium consists of malt extract (1.0%), yeast extract (0.4%), dextrose (0.4%), agar (1.5%) and calcium carbonate (0.15%) in distilled water. With each transfer the agar slant was incubated for 2 weeks at 28° C. To prepare an inoculum for the production phase, the surface growth from the slant culture was transferred to a 500 ml Erlenmeyer flask

TABLE 4

| | In Vivo Antitumor of BMY-40800 Versus P388 Leukemia[a] | | | | | | |
|---|---|---|---|---|---|---|---|
| Expt. No. | Dose, IP (mg/kg/inj) | Treatment Schedule | Median Survival Times (Days) | % T/C | Avg. Weight Change (g) | No. of Mice Alive on Day 5 | No. of Mice Alive on Day 30 |
| 8016 | 1.0 | Days 1–5 | 13.5 | 135 | −0.6 | 4/4 | 0/4 |
| | 0.33 | | 13.5 | 135 | −0.5 | 4/4 | 0/4 |
| | 0.11 | | 11.0 | 110 | 0.4 | 4/4 | 0/4 |
| | Control | | 10.0 | 100 | 2.1 | 10/10 | 0/10 |
| 8023 | 3.2 | Days 1–5 | 7.5 | 75 | −0.9 | 4/6 | 0/6 |
| | 1.6 | | 12.5 | 125 | −0.6 | 6/6 | 0/6 |
| | 0.8 | | 14.0 | 140 | 0.4 | 6/6 | 0/6 |
| | 0.4 | | 13.0 | 130 | 1.1 | 6/6 | 0/6 |
| | Control | | 10.0 | 100 | 1.0 | 10/10 | 0/10 |

[a]Mice were implanted ip with $10^6$ P388 leukemia cells and treatments with BMY-40800 were begun one day later and continued daily for five days. Control mice were given saline injections.

containing 100 ml of sterile medium consisting of glycerol (2%), fish meal (1%) and calcium carbonate (0.5%). This vegetative culture was incubated at 28° C. for 72 hours on a rotary shaker set at 250 rpm. Five mls of the vegetative culture were transferred to a 500 ml Erlenmeyer flask containing 100 ml consisting of the same vegetative medium (glycerol 2%, fish meal 1%, calcium carbonate 0.5%). The production culture was incubated at 28° C. on a shaker such as used for the vegetative culture (250 rpm) for four to five days. BMY-40800 titers, at 96–120 hours, reached 165–180 µg/ml according to HPLC analysis.

B. Fermentor fermentation 100 ml of vegetative culture was prepared as described in Part A. Twenty-five mls of the vegetative culture were transferred into a 2 liter vitro bottle containing 500 mls of the same vegetative medium, and the inoculated culture was incubated at 28° C. on a shaker for 72 hours at 250 rpm. The resulting culture was crossed aseptically into a New Brunswick Microgen fermentor containing 10 liters of the same vegetative medium. The fermentation was carried out at 28° C., aeration of one volume per min and 250 rpm agitation for 120–144 hours. BMY-40800 titers, at 120–144 hours, reached 145–155 µg/ml according to HPLC analysis.

Example 2

Isolation and Purification

A. Preparation of Crude Extract H

Raw fermentation broth (20 L) as obtained by the general procedure of Example 1 was mixed with 20 L ethyl acetate in a 40 L polyethylene bucket (37 cm diameter, 50 cm high) fitted with a polyethylene spigot. The mixture was stirred with an air-driven stirrer at a moderate speed for one hour. To the mixture was added approximately 2L (0.8 Kg) of Dicalite (diatomaceous earth) until it became homogeneous. The mixture was filtered by vacuum filtration using a No. 12 Coors Buchner funnel (33 cm i.d., 35 cm o.d., 12 cm deep). The ethyl acetate phase was separated and evaporated in vacuo to dryness in a rotary evaporator to yield 32.4 g of residue H.

B. Vacuum Liquid Chromatography of Residue H

A Kontes fritted glass Buchner funnel (M Porosity, 150 mL) was packed with 48 g Silica Gel H (Merck) (dry) and the bed equilibrated with hexane-ethyl acetate (1:1). Residue H, 32.4 g., was dissolved in approximately 30 ml ethyl acetate-methanol (9:1), and to the solution was added 5 g Silica Gel H. The mixture was evaporated in vacuo to dryness in a rotary evaporator. The residue was taken up in hexane-ethyl acetate (1:1) (200 mL), the solution poured onto the column and house vacuum applied until sucked dry. The following solvents were used in sequence, 200 mL each of ethyl acetate, chloroform, 1% methanol in chloroform and finally 2% methanol in chloroform. The chromatogram was monitored by TLC using short wavelength UV light and ceric sulfate spray reagent. The desired substance eluted with the chloroform and the 1% and 2% methanol in chloroform. These fractions were pooled (600 mL) and evaporated to dryness in vacuo in a rotary evaporator to yield 2.7 g of Residue I (crude BMY-40800).

C. Silica Gel Column Chromatography of Residue I

An Ace Glass column (4.5 cm o.d. ×43 cm) fitted with a Teflon stopcock was packed with 150 g Woelm Universal Silica Gel (63-200) in chloroform. Residue I was dissolved in chloroform (approximately 10 mL) and applied to the column with a Pasteur pipette. Elution was begun with chloroform (875 mL) followed by 1% methanol in chloroform (1000 mL) and 2% methanol in chloroform (1750 mL total). The chromatogram was followed by TLC using short wavelength UV light and ceric sulfate spray reagent. The fractions containing BMY-40800, which eluted with 2% methanol in chloroform, were combined (500 mL) and evaporated to dryness in vacuo in a rotary evaporator to give 2.4 g of substantially pure BMY-40800.

D. Nicotinamide Purification

The BMY-40800 from Step C above is obtained as a buff-colored amorphous solid. This material may be converted to a white crystalline hydrated material by the following procedure:
1. Vigorously slurry 1 gram of BMY-40800 as obtained according to the procedure of Example 2C in 200–300 ml of 35% w/v nicotinamide-water solution for 2–4 hours at 20°–30° C.
2. With continued rapid slurring increase the temperature of the slurry to 45°–50° C. Stir at 45°–50° C. for 1 to 1.5 hours.
3. Remove heat source and stir rapidly and ambiently for 16–24 hours.
4. Collect the crystals by a filtration (4 cm, fine sintered glass funnel).
5. Under vacuum tamp the crystals to remove cracks or fissures.
6. Wash the crystalline crack-free filter cake with eight 10 ml portions of water to assure complete removal of nicotinamide. Each water washing should be on a crack-free filter cake. Tamp the crystals to remove any cracks or fissures.
7. Maintain vacuum on the filter-cake until all free water appears removed.
8. Vacuum dry the crystals at 25°–40° C. in the presence of phosphorous pentoxide for 16–24 hours. Contemplated yield of product =0.7–0.8 g with an increase in potency (as measured by HPLC) of 15–20% over the material of Step C. Material appears as a crystalline hydrate.

Figure 3:
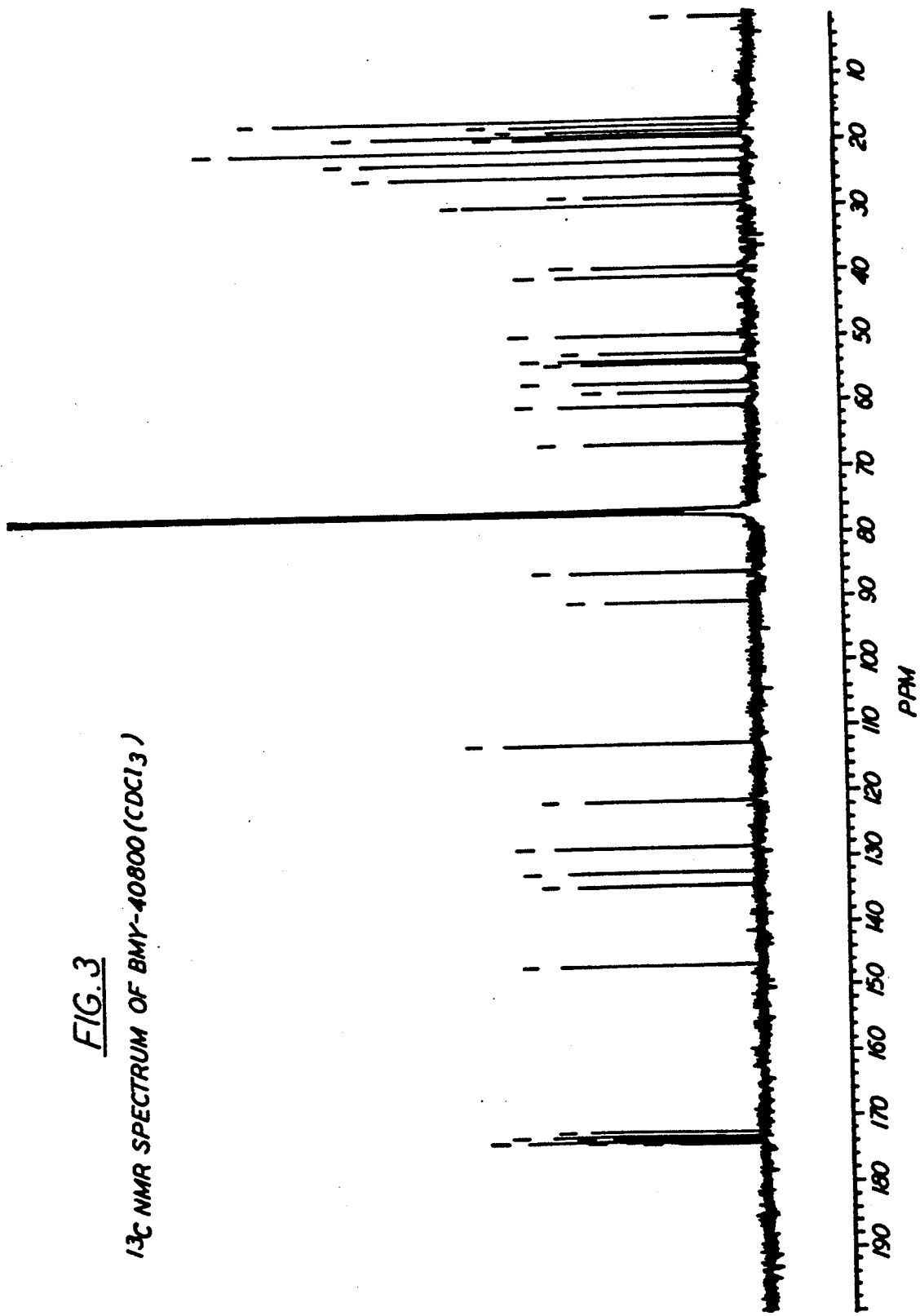
FIG. 3 represents the 90.5 MHz $^{13}C$ magnetic resonance spectrum of BMY-40800 in $CDCL_3$.

What is claimed is:
1. A biologically pure culture of the microorganism *Steptomyces hygroscopias* having all of the identifying characteristics of ATCC 53653, said culture being capable of producing the compound BMY-40800 having the following characteristics:
    (a) a white crystalline solid containing the elements carbon, hydrogen, oxygen, and nitrogen in approximately the following percentages: C, 58.16; H, 6.94; N, 12.84; and O (by difference), 22.26;
    (b) an infrared absorption spectrum (KBr) substantially as shown in FIG. 1;
    (c) a molecular formula of $C_{72}H_{104}N_{14}O_{20}$;
    (d) a 360 MHz proton magnetic resonance spectrum in $CDCl_3$ substantially as shown in FIG. 3;
    (e) a 90.5 MHz $^{13}C$ magnetic resonance spectrum in $CDCl_3$ substantially as shown in FIG. 3;
    (f) exhibits an ultraviolet absorption maximum and absorptivity when dissolved in methanol at a concentration of 0.01538 g/l of 286 nm (a=0.2891);

(g) an apparent molecular weight by FAB mass spectrometry of about 1484;
(h) exhibits in silica gel thin layer chromatography an Rf value of 0.35 with the solvent system chloroform:methanol (95:5 v/v);
(i) exhibits a high performance liquid chromatography retention time of 15 of minutes and a capacity factor $K'=8.9$ with a $C_{18}$ reversed phase silica gel column and the solvent system acetonitrile:tetrahydrofuran:water (4:1:5 v/v); and
(j) is effective in inhibiting the growth of P388 leukemia in mice;

in a recoverable quantity upon aerobic cultivation in an aqueous nutrient medium containing assimilable sources of carbon and nitrogen.

* * * * *